United States Patent [19]

Baldeschwieler et al.

[11] 4,310,505
[45] Jan. 12, 1982

[54] LIPID VESICLES BEARING CARBOHYDRATE SURFACES AS LYMPHATIC DIRECTED VEHICLES FOR THERAPEUTIC AND DIAGNOSTIC SUBSTANCES

[75] Inventors: John D. Baldeschwieler; Ronald C. Gamble, both of Pasadena, Calif.; Marcia R. Mauk, Vancouver, Canada; Tsung-Ying Shen, Westfield; Mitree M. Ponpipom, Branchburg, both of N.J.

[73] Assignee: California Institute of Technology, Pasadena, Calif.

[21] Appl. No.: 92,342

[22] Filed: Nov. 8, 1979

[51] Int. Cl.³ .................... A61K 49/00; A61K 43/00; B01J 13/00
[52] U.S. Cl. ........................................ 424/1; 252/316; 252/319; 424/9; 424/35
[58] Field of Search .................... 424/1, 1.5, 35, 9; 252/316, 319

[56] References Cited

U.S. PATENT DOCUMENTS

| | | | |
|---|---|---|---|
| 3,522,346 | 7/1970 | Chang | 252/316 |
| 3,663,685 | 5/1972 | Evans | 424/1 |
| 3,663,687 | 5/1972 | Evans | 424/1 |
| 3,683,066 | 8/1972 | Ascanio et al. | 424/1 |
| 3,932,657 | 1/1976 | Rahman | 424/319 |
| 3,937,668 | 2/1976 | Zolle | 424/1 X |
| 3,993,754 | 11/1976 | Rahman et al. | 424/177 |
| 4,086,330 | 4/1978 | Petkao et al. | 424/1 |
| 4,089,801 | 5/1978 | Schneider | 252/316 |
| 4,115,536 | 9/1978 | Rothman et al. | 424/1 |
| 4,193,983 | 3/1980 | Ullman et al. | 424/1 X |

OTHER PUBLICATIONS

Gregoriadis, N. Eng. J. Med., vol. 295, Sep. 23, 1976, pp. 704-710.

*Primary Examiner*—Christine M. Nucker
*Attorney, Agent, or Firm*—Joseph E. Mueth

[57] ABSTRACT

Lipid vesicles comprising a lipid bilayer which includes analogs of cell-surface receptors such as dicetyl phosphate; stearylamine; 6-(5-cholesten-3β-yloxy) hexyl 1-thio-β-L-fucopyranoside; 6-(5-cholesten-3β-yloxy) hexyl 1-thio-β-D-galactopyranoside; 6-(5-cholesten-3β-yloxy)hexyl 1-thio-α-D-mannopyranoside; 6-(5-cholesten-3-yloxy)hexyl 2-acetamido-2-deoxy-1-thio-β-D-galactopyranoside; 6-(5-cholesten-3β-yloxy)hexyl 6-amino-6-deoxy-1-thio-β-D-galactopyranoside; or 6-(5-cholesten-3β-yloxy)hexyl 6-amino-6-deoxy-1-thio-α-D-mannopyranoside; cholesterol and distearoyl phospatidylcholine, and an effective amount of physiologically compatible radioactive tracer, cytotoxic or therapeutic agent as a part of the vesicles. The vesicles of this invention can be administered to the human host and have been found to release the contents of the vesicles in a predetermined manner, i.e., controlled release, and in some cases, to be rapidly concentrated in the lymphatic system and/or liver, lungs or spleen of the host.

8 Claims, 7 Drawing Figures

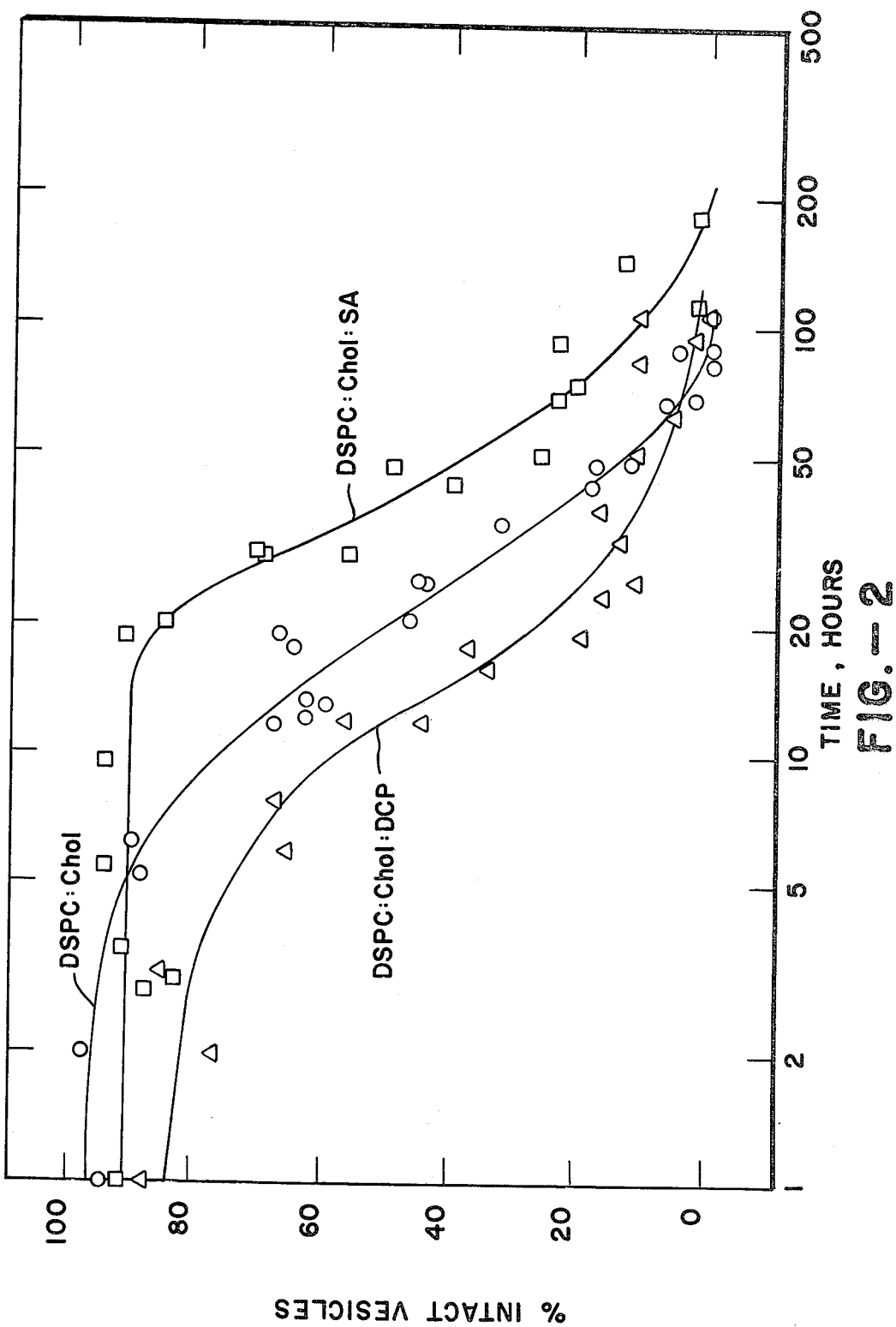

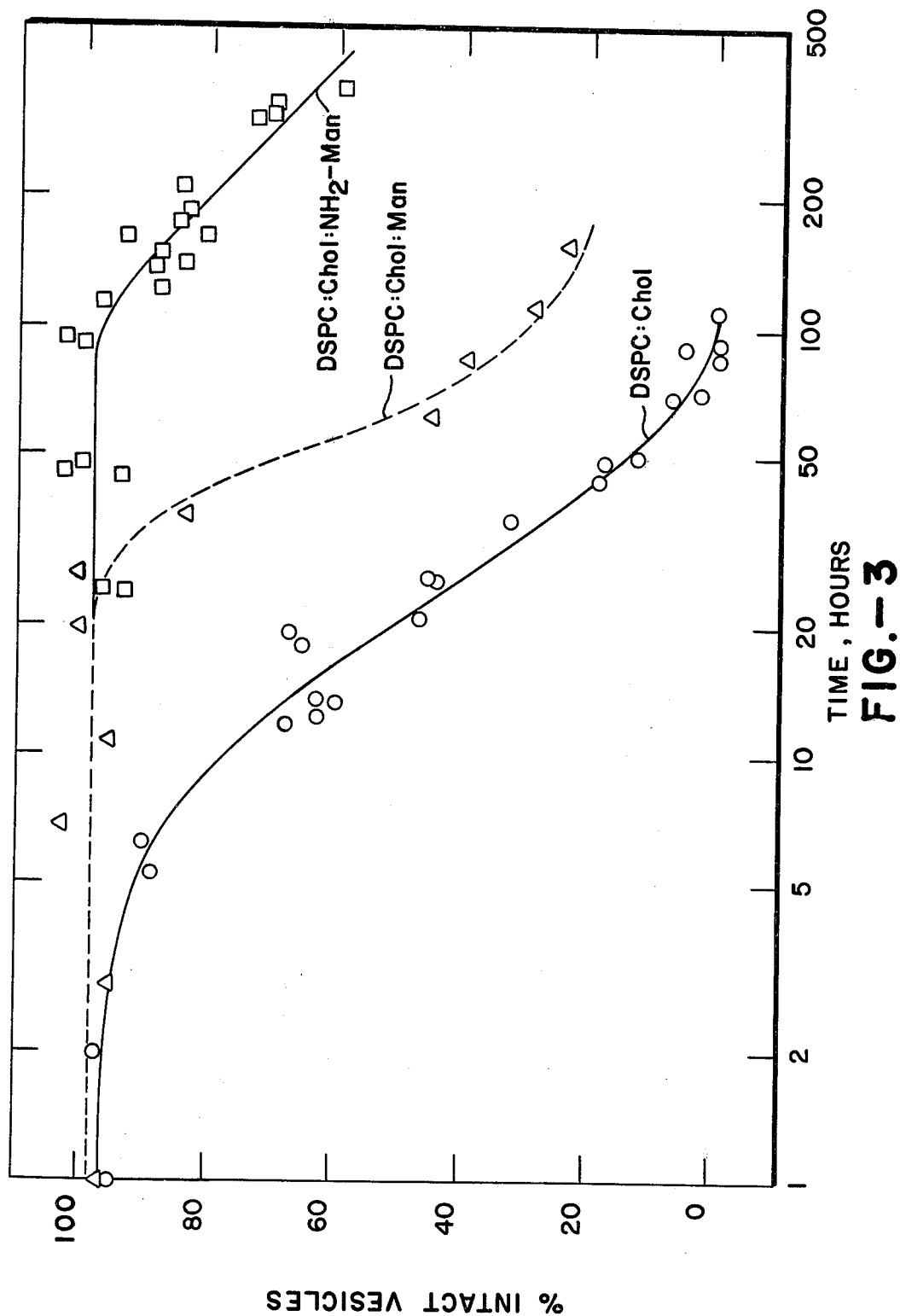

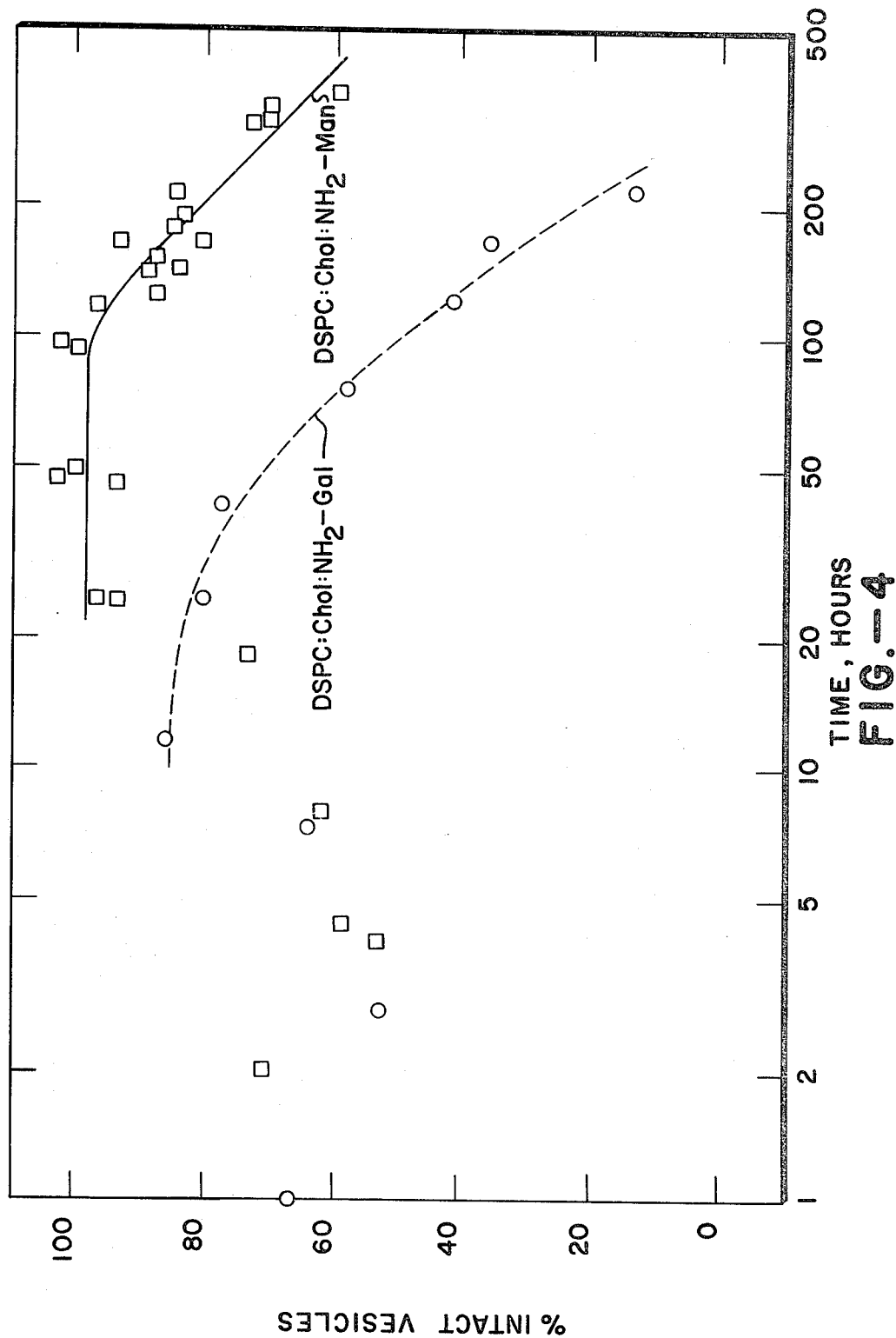
FIG.—4

LIPID VESICLES BEARING CARBOHYDRATE SURFACES AS LYMPHATIC DIRECTED VEHICLES FOR THERAPEUTIC AND DIAGNOSTIC SUBSTANCES

The invention described herein was made in the course of work under grants from the National Institute of Health and National Science Foundation.

BACKGROUND OF THE INVENTION

Lipid vesicles have been previously obtained, and observed through the use of radio-labeled liposomes, McDougall, I. R., Dunnick, J. K., McNamee, M. G., and Kriss, J. P. (1974) *Proc. Natl. Acad. Sci. USA,* 71 3487–3491; Hwang, K. J. and Mauk, M. R. (1977) *Proc. Natl. Acad. Sci. USA,* 74, 4991–4995; Hinkle, G. H., Born, G. S., Kessler, W. V., and Shaw, S. M. (1978) *J. Phar. Sci.* 67, 795–798. These vesicles contain relatively low levels of radioactive ions because of the limited amount of radioactive ions entrapped within the liposomes using simple sonication procedures. The internal aqueous volume of the vesicles is small with the result that only a few percent of the total suspension volume carrying the radioactive ions is encapsulated in the vesicle and the balance is lost for practical purposes.

The preferred ionophore (a generic term intended to imply compounds which are ion-loving or ion attracting) [6S-6α(2S*,3S*), 8β(R*), 9β,11α]-5-(methylamino)-2-[[3,9,11-trimethyl-8-[1-methyl-2-oxo-2-(1H-pyrrol-2-yl)ethyl]-1,7-dioxasporo[5.5]undec-2-yl]methyl]-4-benzoxazolecarboxylic acid, hereinafter referred to as ionophore A23187, has been used to complex and carry divalent cations across natural and artificial lipid membranes, Hyono, A., Hendriks, Th., Daemen, F. J. M., and Bonting, S. L. (1975) *Biochim. Biophys. Acta.,* 389, 34–46; Sarkadi, B., Szasz, I., and Gardos, G. (1976) *J. Membrane Biol.,* 26, 357–370; LaBelle, E. F. and Racker, E. (1977) *J. Membrane Biol.,* 31, 301–315; Pfeiffer, D. R. Taylor, R. W. and Lardy, H. A. (1978) *Ann. N.Y. Acad. Sci.* (in press). Evidence also exists that A23187 can form complexes with trivalent cations, e.g., $La^{+3}$ Pfeiffer, D. R., Reed, P. W., and Lardy, H. A. (1974) *Biochemistry,* 13, 4007–4014.

Gregoriadis and coworkers have labeled liposomes $^{111}$In through use of $^{111}$In-labeled bleomycin, Gregoriadis, G. and Neerunjun, E. D. (1975) *Biochem. Biophys. Res. Comm,* 65, 537–544; Gregoriadis, G. Neerunjun, D. E., and Hunt, R. (1977) *Life Sci.,* 21 357–369. They reported 27–80% of the added radioactivity associated with the phospholipid in negatively charged liposomes and observed 2–4.5% incorporated into positively charged liposomes.

More recently, according to co-pending application Ser. No. 148,102 filed Feb. 22, 1979, there has been discovered a method for routinely loading radioactive ions into lipid vesicles with greater than 90% efficiency. In this method the ionophore is incorporated in the lipid bilayer and is used to carry externally added radioactive ions to a chelator or chelating agent, which was previously entrapped in the vesicles. The binding of the radioactive ion to the chelating agent is sufficiently strong that it provides the driving force for the net transfer of the radioactive ion into the vesicles. These radiolabeled vesicles show more than a 100-fold increase in specific activity over those loaded by simple sonication.

According to this invention, we have found that lipid vesicles wherein the bilayer wall includes cholesterol, distearoyl phospatidylcholine and the various cholesterol derivatives or hydrocarbon compounds with charged hydrophilic headgroups controllably release any drug, or other beneficial agent carried by or within the vesicle. Moreover, certain aminomannose and/or aminogalactose derivatives of cholesterol, have the characteristic upon injection into the host mammal of rapidly and preferentially accumulating in the lymphatic system and/or the lung, spleen or liver. Since these vesicles can be loaded with a wide variety of radioactive tracers and drugs, the vesicles of this invention provide a unique method of delivering a drug to the specific site of a disease. The vesicle wall remains substantially intact for several hours effectively to act as a carrier. Ultimately, the vesicle wall breaks down and releases the drug.

SUMMARY OF THE INVENTION

Briefly, the present invention comprises lipid vesicles comprising a lipid bilayer which includes analogs of cell-surface receptors such as dicetyl phosphate; stearylamine; 6-(5-cholesten-3β-yloxy)hexyl 1-thio-β-L-fucopyranoside; 6-(5-cholesten-3β-yloxy)hexyl 1-thio-β-D-galactopyranoside; 6-(5-cholesten-3β-yloxy)hexyl 1-thio-α-D-mannopyranoside; 6-(5-cholesten-3-yloxy)hexyl 2-acetamido-2-deoxy-1-thio-β-D-galactopyranoside; 6-(5-cholesten-3β-yloxy)hexyl 6-amino-6-deoxy-1-thio-β-D-galactopyranoside; or 6-(5-cholesten-3β-yloxy)hexyl 6-amino-6-deoxy-1-thio-α-D-mannopyranoside; cholesterol and distearoyl phospatidylcholine, and an effective amount of physiologically compatible radioactive tracer, cytotoxic or therapeutic agent as a part of the vesicles.

This invention further comprehends the method comprising administering to the mammalian host lipid vesicles comprising a lipid bilayer which includes analogs of cell-surface receptors such as dicetyl phosphate; stearylamine; 6-(5-cholesten-3β-yloxy)hexyl 1-thio-β-L-fucopyranoside; 6-(5-cholesten-3β-yloxy)hexyl 1-thio-β-D-galactopyranoside; 6-(5-cholesten-3β-yloxy)hexyl 1-thio-α-D-mannopyranoside; 6-(5-cholesten-3-yloxy)hexyl 2-acetamido-2-deoxy-1-thio-β-D-galactopyranoside; 6-(5-cholesten-3β-yloxy)hexyl 6-amino-6-deoxy-1-thio-β-D-galactopyranoside; or 6-(5-cholesten-3β-yloxy)hexyl 6-amino-6-deoxy-1-thio-α-D-mannopyranoside; cholesterol and distearoyl phosphatidylcholine, and an effective amount of physiologically compatible radioactive tracer, cytotoxic or therapeutic agent as a part of the vesicles, said vesicles being further characterized by the controllable release of the carried agent.

It is an object of this invention to provide novel lipid vesicles.

In general, it is an object of this invention to provide lipid vesicles which release radioactive tracers, cytotoxic or therapeutic agents in a controlled and predetermined manner or at a controlled or predetermined time.

More particularly it is an object of one embodiment of this invention to provide novel lipid vesicles having entrapped therein various tracers, drug and therapeutic agents which upon administration to the host mammal will rapidly and preferentially accumulate intact at or within the lymphatic system and/or lung, spleen or liver, and there ultimately releasing said entrapped material.

These and other objects and advantages of this invention will be apparent from the detailed description which follows.

DESCRIPTION OF THE PREFERRED EMBODIMENTS

Figure 1:
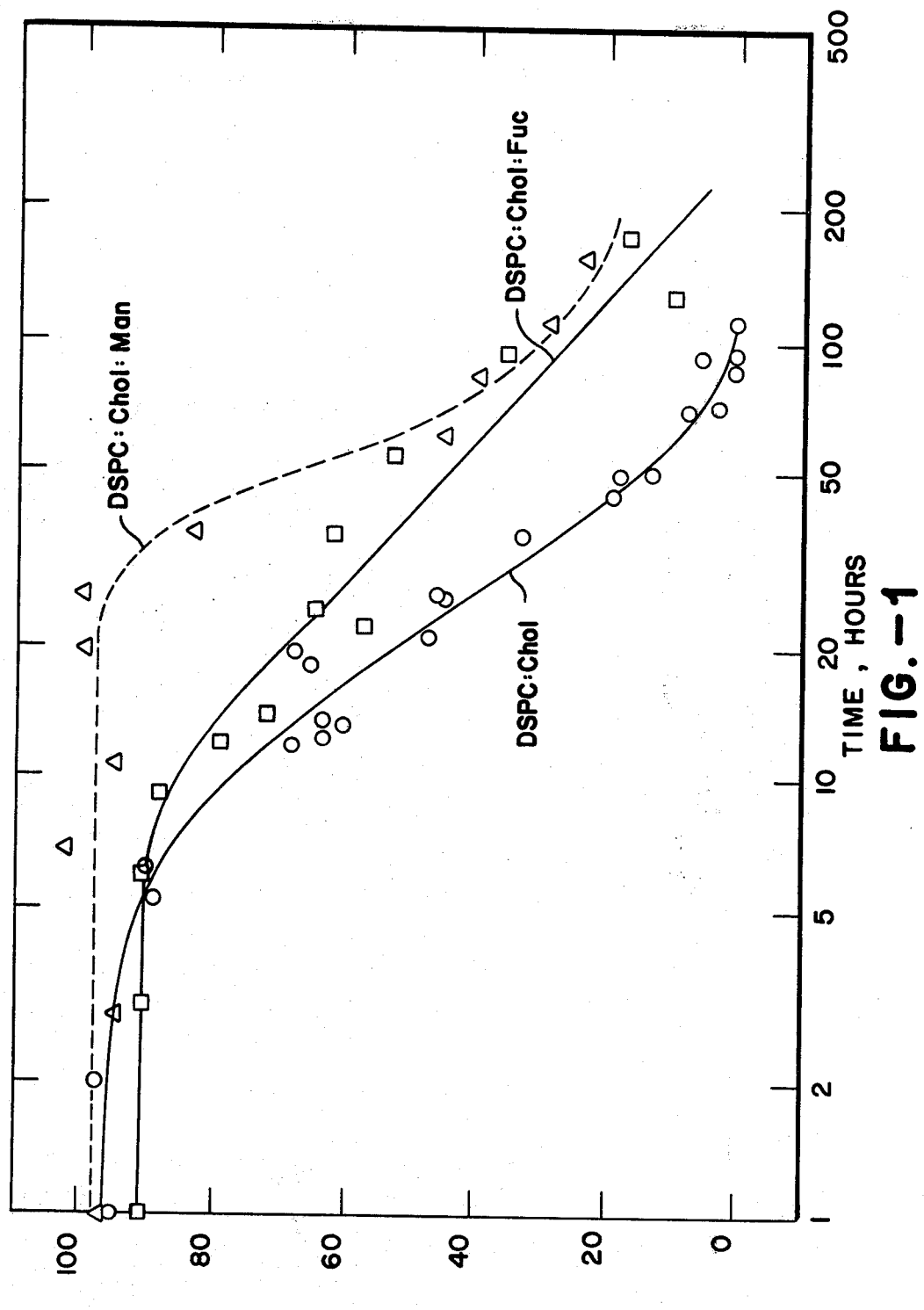

In this patent, the term "vesicles" refers to small sacs containing fluids by encapsulation and/or incorporation within the vesicle wall.

Preferably, the vesicle walls are dicetyl phosphate; stearylamine; 6-(5-cholesten-3β-yloxy)hexyl 1-thio-β-L-fucopyranoside; 6-(5-cholesten-3β-yloxy)hexyl 1-thio-β-D-galactopyranoside; 6-(5-cholesten-3β-yloxy)-hexyl 1-thio-α-D-mannopyranoside; 6-(5-cholesten-3-yloxy)hexyl 2-acetamido-2-deoxy-1-thio-β-D-galactopyranoside; 6-(5-cholesten-3β-yloxy)hexyl 6-amino-6-deoxy-1-thio-β-D-galactopyranoside; or 6-(5-cholesten-3β-yloxy)hexyl 6-amino-6-deoxy-1-thio-α-D-mannopyranoside; cholesterol and distearoyl phospatidylcholine, and an effective amount of physiologically compatible radioactive tracer, cytotoxic or therapeutic agent as a part of the vesicles.

It is to be understood that the above-identified ionophore can also be present when the vesicle carries a radioactive cation. In such embodiment, a chelator can also be present within the vesicle, and preferably is nitrilotriacetic acid (NTA). However, other chelators for polyvalent metal ions such as ethylene diamine tetra-acetic acid can be used. When the vesicles carry other agents such as organic materials like pharmaceuticals, the use of the ionophore and chelating agent is unnecessary.

The vesicles can be carried or be loaded with a variety of materials including enzymes for enzyme replacement therapy, hormones, radionuclides, cell-modifying agents, antigens, antibodies, interferon inducers, virus subunit particles, genetic material such as RNA and DNA, and drugs and pharmaceuticals generally. Thus, by way of example, the vesicles can carry antitumor drugs such as methotrexate and actinomycin for cancer chemotherapy. The vesicles of this invention can also be used for glycogen storage disease therapy using amyloglucosiases entrapped within the vesicles.

Obviously, the vesicles which have an affinity for the lymphatic system can be used for the diagnosis and treatment of tumors and metastises of the lymphatic system.

The radioisotopes such as $Tc^{99m}$ can be used for diagnostic purposes when loaded within the vesicles.

The vesicles are also used in the treatment of lysosomal storage diseases for filling target cells, the elimination of undesirable materials in extracellular spaces, and the modification of cellular structure and activity.

It is to be understood that the radioactive tracer, cytotoxic or therapeutic agent, sometimes herein simply the "carried agent", can be encapsulated by the vesicle walls. Alternatively, the carried agent can be a part of, that is, dispersed or dissolved in the vesicle wall-forming materials.

The incorporation of the carried agent within the vesicle can be accomplished in a variety of ways.

One method which is generally applicable to water soluble and stable agents is to dissolve the agent in water, usually under isotonic conditions, add the various vesicle wall-forming ingredients and to subject the mass to sonication.

Water soluble carried agents can also be incorporated into the vesicles of this invention by the procedure of Szoka et al, *Proc. Natl. Acad. Sci.*, 75, 4194–4198 (1978). This procedure is particularly useful for fragile water-soluble materials such as enzymes and hormones.

Lipophilic carried agents can be incorporated by sonicating the vesicles and then adding the lipophilic carried agent. This procedure is more fully described in Huang et al, *Biochemistry*, 18, 1702–1707 (1979). Immunoglobulin G is an example of a lipophilic carried agent which becomes incorporated in the vesicle wall by this procedure.

The following examples are presented solely to illustrate the invention, and are not intended to be limiting in any way. In the examples, the parts and percentages are by weight unless otherwise indicated.

EXAMPLE I

Unilamellar vesicles with A23187 incorporated into the bilayer were prepared using the cholesterol derivatives (or DCP or SA) listed in Table 1. In a typical preparation, the cholesterol derivative, along with free cholesterol, DSPC and A23187 (0.04 μmol) were dissolved in chloroform, dried to a thin film at 60° under a stream of nitrogen, and then dried in vacuo overnight. Where appropriate, 1 μCi of tritiated cholesteryl oleate (specific activity 11 μCi/μg) was included in the mixture as a marker for the lipid phase. The dried lipids were then rehydrated with 0.5 ml of 1 mM NTA in phosphate buffered saline (PBS), which is 0.9% NaCl, 5 mM sodium phosphate, pH 7.4. The mixture was sonicated in a glycerol bath which was initially at room temperature (Branson sonicator with titanium microtip, high power setting) until the solution cleared (approximately 5 minutes). Following sonication the vesicles were incubated at 60° for 10 minutes to anneal any structural defects. The vesicle suspension was then centrifuged at 300×g to remove titanium fragments and highly aggregated material. The NTA external to the liposomes was then removed by passage of the preparation over a 0.8×35 cm column of Sephadex G-50 which was equilibrated with PBS and conditioned by previous passage of lipid vesicles to saturate the irreversible binding sites. The vesicles eluted in the void volume of the column with typically a four-fold dilution and 95% recovery based on the tritiated cholesteryl oleate marker.

EXAMPLE II

Loading Procedure

After Sephadex chromatography, the vesicle preparations were loaded with $^{111}In^{3+}$ using incubation mixtures consisting typically of 500 μl of vesicles, 35 μl of 3.4 μM InCl₃ in 104 mM sodium citrate (pH 7.4) and 1–50 μl of $^{111}In^{3+}$ in 2 mM HCl, depending on the required activity. A volume of two times PBS equal to that of the $^{111}In^{3+}$ addition was included in the incubation mixture. Incubation time and temperature varied with vesicle composition as indicated below. The incubations were terminated by adding 50 μl of 10 mM EDTA (ethylene diamine tetracetic acid) in PBS and immediately chromatographing the mixture on Sephadex G-50 equilibrated with PBS. The EDTA picks up residual indium on the outside of the vesicles so that the column does not become radioactive. In the results presented below A23187 was used to achieve loading of lipid vesicles with $^{111}In^{3+}$.

When vesicles are disrupted in vivo, $^{111}In^{3+}$-NTA complex is released, and $^{111}In^{3+}$ is available to bind to nearby macromolecules. Binding of $^{111}In^{3+}$ to a macromolecule causes a large change in the effective molecular rotational correlation time at the site of the indium nucleus, and consequently there is a decrease in the time-integrated angular correlation factor, $<G_{22}(\infty)>$. The $<G_{22}(\infty)>$ value can thus be used to monitor the extent of breakup of vesicles; its value ranges from ~0.62 for $^{111}$In-NTA contained in intact vesicles to 0.18 for the ion bound to serum proteins. The stability and permeability of the vesicles containing $^{111}$In-NTA complex were also checked by the PAC technique. For all systems listed in Table 1, the $<G_{22}(\infty)>$ values remained high after incubation at 37° for 0.5 hr. in the presence of heat-inactivated calf serum. On distruption of the vesicles by a small addition of isopropanol, the $<G_{22}(\infty)>$ dropped to the value expected for $^{111}$In$^{3+}$ binding to serum proteins.

In FIGS. 1 through 4 there is shown the "intactness" of the vesicles of this invention as determined by PAC. In some cases, the vesicles of this invention are compared with vesicles having various other bilayer compositions.

Figure 5A:
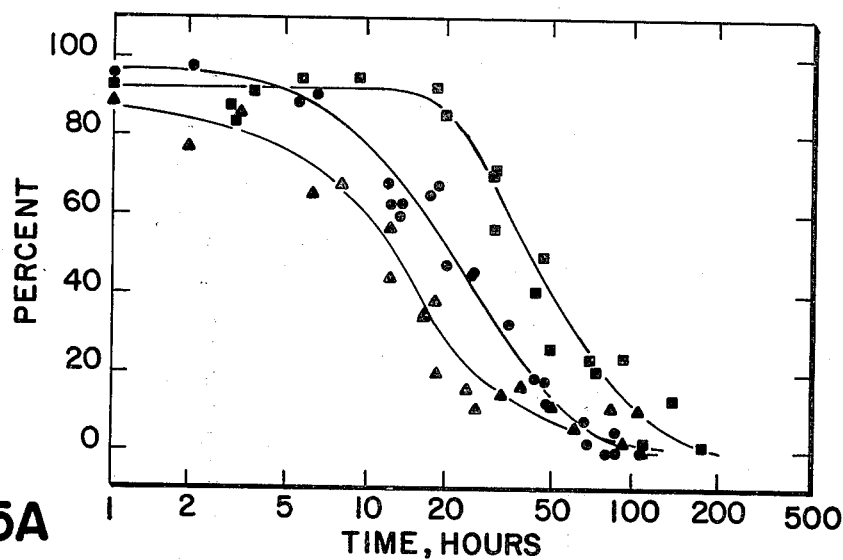
Figure 5B:
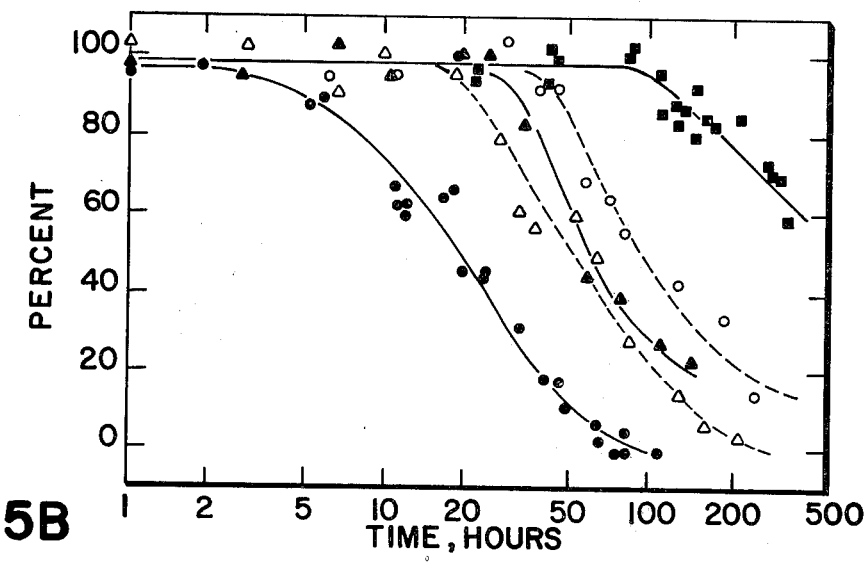
Figure 5C:
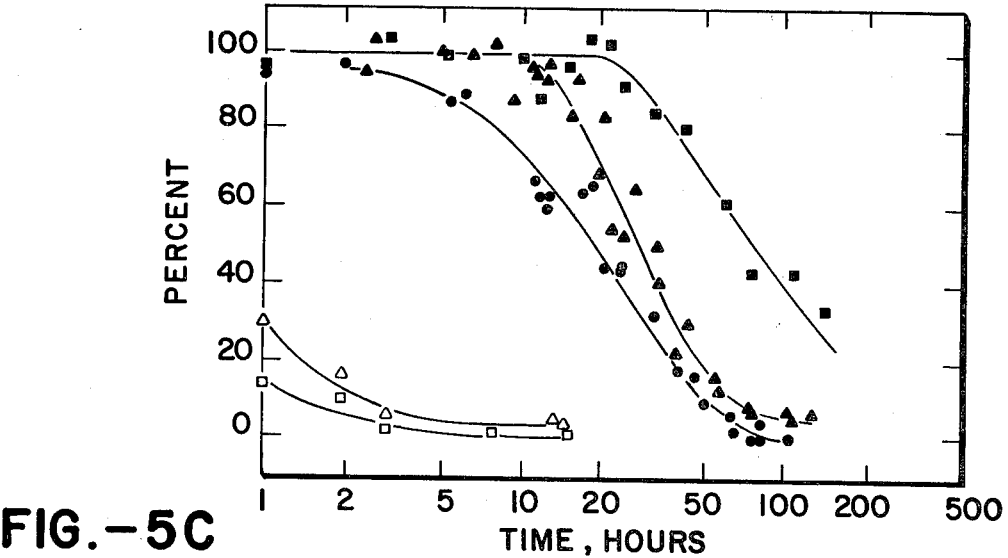

FIGS. 5a–5c show the effect of different variables.

EXAMPLE III

For in vivo studies, vesicles containing $^{111}$In-NTA were injected subcutaneously into Swiss-Webster mice (18–22 g) near the midline of the back at the level of the scapulae. At appropriate times the mice were killed and PAC measurements were immediately made on the portions of skin tissue which showed significant radioactivity. The amounts of radionuclide in all organs and tissues were determined using a well-type gamma counter.

The stability of subcutaneously administered vesicles is affected by surface charge (FIG. 5a and Table 1). Negatively-charged vesicles (dicetyl phosphate), indicated by Δ, exhibit a shorter life-time than the control DSPC:Chol vesicles, while positively-charged vesicles (stearylamine), indicated by □, show an enhanced halftime. The presence of neutral sugars on the vesicle surface increases the in vivo lifetime to an even greater extent. Table 1 shows the increased stability observed for fucose, galactose, mannose, and acetamidogalactose derivatives of cholesterol.

The changes in in vivo vesicle behavior resulting from the presence of amino-sugar derivatives of cholesterol are most dramatic. The half-times for vesicles bearing the aminogalactose and aminomannose derivatives are substantially longer—100 and 600 hr respectively (Table 1 and FIG. 5b), indicated by circular points, than the half-times for other derivatives.

Mice were injected subcutaneously with vesicles entrapping $^{111}$In-NTA complex suspended in 0.20 ml of PBS. The vesicles consisted of DSPC:Chol:NH$_2$-Man:A23187 or DSPC:Chol:NH$_2$-Gal:A23187. The site of injection was on the dorsal side of the animal at the midline of the body at approximately the level of the shoulder blades.

Radioactivity was not located at the site of injection as is observed with other vesicle compositions. Radioactivity was found primarily (1) in the skin on the lateral area of the mouse immediately posterior to the forelegs (i.e., the "armpit" area), or (2) occasionally in the skin of the neck at the base of the skull. The pattern of removal of the vesicles from the site of injection is as expected for drainage via the lymphatic channels to regional lymph nodes.

A moist appearing, blister-like welt in the previously described armpit location was visible to the unaided eye within one hour after injection. With unilamellar vesicles the swelling persisted up to 8 hours after injection, with multilamellar vesicles up to 22 hours.

The welts observed following injection correspond to the location of the radioactivity. The pattern observed in the autoradiogram shows that the welt does not represent intact migration of the injection bolus. The radioactivity is confined within discrete fibers or vessels.

The injected radioactivity is rapidly concentrated such that the radioactive tissue comprises less than 65% of the original injection volume. Measurements of $<G_{22}(\infty)>$ values on portions of skin containing radioactivity show an initial decline (at $<\sim18$ hours) not observed with other vesicle systems (FIG. 4). This decline arises from a geometry effect in the PAC spectrometer. For example, reduction of sample size from a sphere of 200 μl volume to a sphere of 75 μl volume results in a 25% reduction in the $<G_{22}(\infty)>$ value. Since the PAC values reflect only the geometry of the radioactive portion and not the geometry of the total piece of tissue analyzed, concentration of the vesicles to a small area within a piece of tissue would result in the "artifactual" decrease in percentage of intact vesicles.

For all other vesicle systems examined, no areas of localized swelling are observed and the vesicles remain associated with the skin at the site of injection. It will be understood by those skilled in the art that those vesicles containing carried agents which remain associated with the injection site are also of major beneficial importance since the vesicles gradually release the contained carried agent over a prolonged time period. This is shown by the data of Table 2.

The effects observed with the aminomannose derivative of cholesterol are found to be dose dependent (Table 1 and FIG. 5b), open circles and open triangles. Decreasing the proportion of aminomannose derivative reduces the in vivo lifetime and decreases the extent of blister formation. For vesicles of DSPC:Chol:NH$_2$Man in the molar ratios 2:0.9:0.1, localized swelling is not apparent. Combining the mannose derivative of cholesterol with stearylamine does not produce the effects observed with the aminomannose derivative (Table 1). The vesicles bearing the combined groups remain at the site of injection and do not migrate to or concentrate to the rear of the forelegs as observed for the amino-sugar bearing vesicles. Therefore the specificity observed with the amino-sugar derivatives is a result of the stereochemistry of the surface groups and is not a simple additive effect of sugar+charge. The foregoing data show that an NH$_2$ group positioned on a mannose or galactose residue confers substantial specificity for the lymphatic system when vesicles are administered subcutaneously.

An important factor to be considered in developing vesicle systems capable of providing controlled delivery of therapeutic agents is the accessibility of the released material to a given cellular or subcellular site, in particular, whether the entrapped material is released intra- or extra-cellularly. To obtain such information the in vivo behavior of the indium complexes of ethylenediaminetetraacetic acid [($^{111}$In-EDTA$^{-1}$] and diethylenetriaminepentaacetic acid [($^{111}$In-DTPA)$^{-2}$] was examined. These indium complexes are very stable (13), and when administered subcutaneously are rapidly cleared from circulation by the kidneys. In fact, greater than 90% of the ($^{111}$In-EDTA)$^{-1}$) and ($^{111}$IN-DTPA)$^{-2}$ administered in this way is excreted within 2.4 and 1.4 hr, respectively (FIG. 5c), open squares and open triangles. FIG 5c also shows the effect of the vesicle encapsulation on the rate of excretion of the complexes. For DSPC:Chol vesicles elimination of ($^{111}$In-EDTA)$^{-1}$ lags by about 8 hrs the destruction of the vesicles as measured by the PAC technique on preparations containing $^{111}$In-NTA. The delayed excretion of the ($^{111}$In-EDTA)$^{-1}$ complex, indicated by triangles, and ($^{111}$In-DTPA)$^{-2}$, indicated by squares, complex suggests that the vesicles may be destroyed within a cell or compartment. Prolonged delay in excretion of ($^{111}$In-DTPA)$^{-2}$ (FIG. 5c) is consistent with this hypothesis, since membrane permeability should decrease with increasing charge on the complex. For all systems studied a delay is observed between the time of injection and the onset of vesicle destruction (FIGS. 5a and 5b).

The in vivo half-time of vesicle destruction can be varied over a 50-fold range by the inclusion in the lipid bilayer of various hydrocarbon compounds with charged head-groups or sugar and amino-sugar derivatives of cholesterol. This provides means for controlled deposition and release of therapeutic agents by subcutaneous injection. In combination with the timed release feature, localization of vesicles in lymphoid tissue allows visualization and treatment of tumors and metastases of the lymphatic system. In addition, PAC observations combined with tissue distribution studies of vesicles containing stable indium complexes provides valuable insight into the mechanisms of vesicle metabolism. The highly stereospecific effect of the sugar derivatives in targeting the phospholipid vesicles is a major advance in the art.

TABLE 1

Each subcutaneous injection of lipid vesicles typically contains 1.0 mg total lipid, 20 μCi $^{111}$In$^{3+}$ bound to 1 mM NTA inside and phosphate-buffered saline (0.9% NaCl, 5 mM sodium phosphate, pH 7.4) inside and outside of the vesicles. Total injection volume is 200 μl. Data is based on PAC measurements of the skin. The 100% intact level corresponds to the $<G_{22}(\infty)>$ value of the vesicles prior to injection; 0% intact corresponds to the $<G_{22}(\infty)>$ of $^{111}$In$^{3+}$ bound to serum proteins.

| Composition (molar ratio) | Time (hrs.) that given percentages of vesicles are intact | | |
|---|---|---|---|
| | 80% | 50% | 20% |
| DSPC:Chol (2:1) (Control) | 9 | 21 | 43 |
| DSPC:Chol:DCP (2:0.5:0.5) | 3 | 12 | 25 |
| DSPC:Chol:SA (2:0.5:0.5) | 24 | 41 | 78 |
| DSPC:Chol:Fuc (2:0.5:0.5) | 13 | 41 | 120 |
| DSPC:Chol:Gal (2:0.5:0.5) | 28 | 57 | 117 |
| DSPC:Chol:Man (2:0.5:0.5) | 42 | 64 | 170 |
| DSPC:Chol:AcAmGal (2:0.5:0.5) | 43 | 84 | 170* |
| DSPC:Chol:NH$_2$Gal (2:0.5:0.5) | 35 | 100 | 210 |
| DSPC:Chol:NH$_2$Man (2:0.5:0.5) | 200 | 600* | |
| DSPC:Chol:NH$_2$Man (2:0.75:0.25) | 55 | 95 | 250 |
| DSPC:Chol:NH$_2$Man (2:0.9:0.1) | 30 | 55 | 120 |
| DSPC:Chol:Man:SA (2:0.5:0.25:0.25) | 26 | 70 | 200* |

*Extrapolated value.

DSPC = distearoyl phospatidylcholine
Chol = cholesterol
DCP = dicetyl phosphate
SA = stearylamine
Fuc = 6-(5-cholesten-3β-yloxy)hexyl 1-thio-β-L-fucopyranoside.
Gal = 6-(5-cholesten-3β-yloxy)hexyl 1-thio-β-D-galactopyranoside.
Man = 6-(5-cholesten-3β-yloxy)hexyl 1-thio-α-D-mannopyranoside.
Ac Am Gal = 6-(5-cholesten-3-yloxy)hexyl 2-acetamido-2-deoxy-1-thio-β-D-galactopyranoside.
NH$_2$Gal = 6-(5-cholesten-3β-yloxy)hexyl 6-amino-6-deoxy-1-thio-β-D-galactopyranoside.
NH$_g$ Man = 6-(5-cholesten-3β-yloxy)hexyl 6-amino-6-deoxy-1-thio-α-D-mannopyranoside.

TABLE 2

| | Tissue distribution of recovered $^{111}$In$^{3+}$ following subcutaneous injection of vesicles. | | | | | | | | | | | | |
|---|---|---|---|---|---|---|---|---|---|---|---|---|---|
| | DSPC:Chol:A23187(Control) | | | DSPC:Chol:DCP:A23187 | | | | DSPC:Chol:SA:A23187 | | | DSPC:Chol:Gal:A23187 | | |
| Hrs | 0–24 | 24–72 | >72 | 0–12 | 12–24 | 24–72 | >72 | 0–24 | 24–72 | >72 | 0–24 | 24–72 | >72 |
| Tissue | | | | | | | | | | | | | |
| Blood | 1.0 | 0.2 | 0.2 | 1.5 | 1.7 | 0.3 | 0.1 | 0.5 | 0.4 | 0.5 | 0.8 | 0.2 | 0.1 |
| Heart | 0.04 | 0.05 | 0.06 | 0.05 | 0.09 | 0.06 | 0.1 | 0.02 | 0.03 | 0.07 | 0.03 | 0.04 | 0.04 |
| Lung | 0.1 | 0.02 | 0.02 | 0.1 | 0.3 | 0.1 | 0.4 | 0.03 | 0.06 | 0.13 | 0.05 | 0.05 | 0.06 |
| Liver | 2.5 | 3.5 | 8.7 | 1.9 | 7.8 | 7.1 | 11.9 | 0.3 | 1.7 | 4.1 | 2.1 | 4.5 | 6.1 |
| Spleen | 0.1 | 0.2 | 0.6 | 0.3 | 0.9 | 0.6 | 1.5 | 0.1 | 0.1 | 0.3 | 0.07 | 0.2 | 0.2 |
| Kidney | 0.2 | 0.6 | 0.8 | 0.3 | 0.7 | 0.8 | 0.9 | 0.2 | 0.8 | 1.2 | 0.3 | 0.5 | 0.6 |
| Stomach | 0.1 | 0.1 | 0.1 | 1.2 | 0.2 | 0.2 | 0.2 | 0.9 | 0.1 | 0.2 | 0.06 | 0.09 | 0.1 |
| Small Int. | 0.8 | 1.0 | 1.5 | 1.2 | 2.6 | 2.2 | 2.5 | 0.5 | 0.9 | 1.1 | 0.7 | 1.1 | 1.0 |
| Large Int. | 0.6 | 0.4 | 0.7 | 0.5 | 1.1 | 0.9 | 1.2 | 0.8 | 0.5 | 0.9 | 0.5 | 0.5 | 0.4 |
| Brain | a | a | 0.01 | 0.02 | 0.03 | 0.01 | 0.02 | a | 0.01 | 0.02 | 0.02 | 0.01 | 0.01 |
| Abd. Tis. | 7.0 | 6.5 | 10.9 | 5.8 | 5.9 | 9.5 | 10.2 | 7.1 | 7.3 | 6.3 | 4.0 | 3.5 | 5.5 |
| Chest Tis. | 10.7 | 12.3 | 7.4 | 11.1 | 14.9 | 7.2 | 11.7 | 11.1 | 12.1 | 13.1 | 15.3 | 17.3 | 16.8 |
| Extremities | 0.5 | 1.6 | 1.6 | 3.4 | 2.5 | 4.6 | 4.4 | 0.5 | 0.8 | 1.2 | 0.6 | 1.7 | 1.5 |
| Skull | 0.6 | 0.9 | 1.0 | 0.6 | 1.9 | 1.5 | 1.9 | 0.3 | 0.8 | 1.5 | 0.7 | 1.7 | 1.6 |
| Skin[b] | 76.2 | 72.7 | 66.4 | 72.7 | 60.2 | 63.1 | 53.0 | 78.0 | 74.7 | 69.8 | 73.4 | 68.9 | 66.0 |
| | ±8.3 | ±3.8 | ±4.0 | ±8.6 | ±4.6 | ±6.3 | ±5.7 | ±14.1 | ±11.3 | ±7.1 | ±5.4 | ±3.2 | ±9.2 |
| % Recovery | 97 | 99 | 104 | 96 | 98 | 101 | 95 | c | c | 102 | 100 | 102 | 90 |
| # Mice | 13 | 8 | 4 | 7 | 5 | 5 | 4 | 8 | 7 | 5 | 9 | 4 | 4 |

[a]Value less than 0.01
[b]Values for skin include ± S.E.M.
[c]Value was not determined.

TABLE 3

| | Tissue distribution of recovered $^{111}In^{3+}$ following intravenous injection of vesicles | | | | | | | | | | |
|---|---|---|---|---|---|---|---|---|---|---|---|
| | DSPC:Chol:A23187 | | | DSPC:Chol: DCP:A23187 | | DSPC:Chol: SA:A23187 | | DSPC:Chol:Gal:A23187 | | DSPC:Chol:NH$_2$ Man:A23187 | | |
| Hrs | 1 | 3 | 24 | 3 | 24 | 3 | 24 | 3 | 24 | 1 | 3 | 24 |
| Tissue | | | | | | | | | | | | |
| Blood$^a$ | 85.5 | 54.4 | 6.0 | 38.4 | 6.5 | 28.1 | 5.9 | 38.2 | 2.0 | 2.1 | 1.0 | 0.3 |
| | ±0.5 | ±9.2 | +3.0 | ±4.9 | ±2.1 | ±7.1 | ±1.7 | ±6.5 | ±1.8 | ±0.5 | ±0.2 | ±0.1 |
| Heart | 1.3 | 1.2 | 0.5 | 0.7 | 0.5 | 0.4 | 0.5 | 0.7 | 0.4 | 0.8 | 0.1 | 0.1 |
| Lung$^a$ | 1.8 | 2.6 | 1.4 | 1.3 | 0.6 | 1.9 | 0.6 | 1.5 | 0.6 | 24.0 | 5.9 | 1.2 |
| | ±0.5 | ±1.6 | ±1.2 | ±0.2 | ±0.1 | ±0.9 | ±0.1 | ±0.0 | ±0.2 | ±5.2 | ±3.8 | ±0.4 |
| Liver$^a$ | 12.2 | 20.4 | 31.0 | 16.8 | 21.4 | 54.3 | 52.0 | 18.2 | 37.5 | 31.8 | 66.9 | 65.8 |
| | ±0.1 | ±3.6 | ±10.0 | ±5.8 | ±3.7 | ±3.1 | ±6.4 | ±2.1 | ±8.8 | ±3.8 | ±8.3 | ±1.0 |
| Spleen | 1.4 | 2.3 | 4.2 | 3.2 | 2.0 | 3.3 | 2.3 | 1.5 | 2.4 | 3.5 | 7.4 | 8.5 |
| Kidney | 2.7 | 2.9 | 2.8 | 3.2 | 4.4 | 1.7 | 2.0 | 2.8 | 4.2 | 4.6 | 1.8 | 1.8 |
| Stomach | 0.6 | 0.7 | 0.9 | 0.5 | 1.4 | 0.5 | 0.5 | 0.5 | 0.7 | 0.7 | 0.2 | 0.2 |
| Small Int. | 4.6 | 7.5 | 11.0 | 8.1 | 14.4 | 4.7 | 4.9 | 8.5 | 10.6 | 5.2 | 1.6 | 1.2 |
| Large Int. | 1.1 | 2.6 | 4.0 | 3.4 | 4.5 | 1.4 | 1.3 | 2.9 | 3.7 | 1.7 | 0.8 | 0.8 |
| Brain | 0.5 | 0.5 | 6 | 0.4 | 0.1 | 0.3 | 0.1 | 0.4 | 6 | 0.2 | $^b$ | $^b$ |
| Abd. Tis. | 9.8 | 8.6 | 9.5 | 10.6 | 10.4 | 6.0 | 6.4 | 10.8 | 9.9 | 7.0 | 3.8 | 5.7 |
| Chest Tis. | 10.0 | 9.2 | 6.2 | 9.9 | 8.9 | 5.4 | 6.1 | 10.2 | 7.0 | 7.0 | 3.1 | 4.2 |
| Extremeties | 6.1 | 5.7 | 9.1 | 7.5 | 7.7 | 3.7 | 9.3 | 8.9 | 7.4 | 3.3 | 3.4 | 5.4 |
| Skull | 8.3 | 7.8 | 5.9 | 7.3 | 8.1 | 4.1 | 4.1 | 7.5 | 5.3 | 4.0 | 1.9 | 2.7 |
| Skin | 4.7 | 7.0 | 11.0 | 11.0 | 13.6 | 5.1 | 6.9 | 12.0 | 9.8 | 5.5 | 2.7 | 2.2 |

$^a$Values for blood, lung and liver include ± S.E.M.
$^b$Value less than 0.1

EXAMPLE IV

In this Example, the vesicles are injected intravenously. The data of Table 3 shows that the NH$_2$Man derivative is preferentially accummulated, that is, targeted, initially for the lung, and after 3 and 24 hours, for the liver and spleen, the latter being the body's largest lymphatic organ.

It is to be understood that the loaded vesicles can be administered in any conventional way using pharmaceutically acceptable carriers. Thus, oral and parenteral forms of dosage may be used.

EXAMPLE V

Following the method of Examples I-II, loaded lipid vesicles of the following compositions are prepared.

TABLE 4

| Bilayer Composition (Mole Ratio) | Carried Agent |
|---|---|
| DSPC:Chol:AcAmGal (2:0.5:0.5) | Methotrexate |
| DSPC:Chol:NH$_2$Gal (2:0.5:0.5) | Actinomycin |
| DSPC:Chol:NH$_2$Man (2:0.5:0.5) | Tc$^{99m}$ |

The following examples describe the preparation of certain cell-surface acceptors used in the practice of this invention.

EXAMPLE VI

6-Deoxy-1,2:3,4-di-O-isopropylidene-6-phthalimido-α-D-galactose

Potassium phthalimide (4.94 g.) is added to a solution of 6-deoxy-6-iodo-1,2:3,4-di-O-isopropylidene-α-D-galactose (9.0 g.) in N,N-dimethylformamide (50 ml.). The suspension is heated with stirring for 8 hours at 130° C. (bath temperature). Another batch of potassium phthalimide (1.25 g.) is added to the cooled brown solution which is then heated with stirring for another 8 hours at the same temperature. The solution is evaporated in vacuo to a dark syrup which is partitioned between ethyl ether and water. The dark insoluble material is filtered and discarded, and the ethereal layer is washed three times with water, dried, and evaporated to a syrup (consisting of the product and the starting material). This mixture is separated by column chromatography on silica gel with 5% ethyl acetate in chloroform as eluant. The title compound is isolated as a crystalline material which is recrystallized from methanol to give 5.1 g. (54%) of the product, m.p., 138°–141° C.; [lit. m.p. 144.5°–145.5° C.]; n.m.r. (chloroform-d) ∂ 5.42 (d, J$_{1,2}$ 5.0 Hz, H-1), 7.47–7.82 (4 aromatic), 1.23, 1.37, 1.43, and 1.52

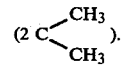

EXAMPLE VII

6-Deoxy-6-phthalimido-D-galactopyranose

A solution of 6-deoxy-1,2:3,4-di-O-isopropylidene-6-phthalimido-α-D-galactose (5.0 g.) in glacial acetic acid (50 ml.) and water (18 ml.) is heated for 32 hours at 80° C. (bath temperature). The solution is filtered and the filtrate is evaporated in vacuo to a crystalline mass. Recrystallization from absolute ethanol affords the title compound (3.0 g., 76%), m.p. 155° C. (dec.), softened at 95° C.

EXAMPLE VIII

Step A:
1,2,3,4-Tetra-O-acetyl-6-deoxy-6-phthalimido-D-galactopyranose

6-Deoxy-6-phthalimido-D-galactopyranose (2.9 g.) is acetylated with acetic anhydride (12 ml.) in pyridine (20 ml.) in the normal manner to give 1,2,3,4-tetra-O-acetyl-6-deoxy-6-phthalimido-D-galactopyranose (4.30 g., 96%) as a mixture of α- and β-anomers in the ratio of 1:1.6, [α]$_D^{27}$ +52.5° C. (C 1.0, chloroform); n.m.r. (chloroform-d): ∂ 5.70 (d, J$_{1,2}$ 8.0 Hz, H-1β), 6.33 (b, H-1α).

Step B:
2,3,4-Tri-O-acetyl-6-deoxy-6-phthalimido-α-D-galactopyranosyl bromide

A solution of 1,2,3,4-tetra-O-acetyl-6-deoxy-phthalimido-D-galactopyranose (4.2 g.) in dichloromethane (2 ml.) is treated with 30–32% hydrobromic acid in glacial acetic acid (10 ml.) for 1 hour. The reaction mixture is poured into ice-water, and the product is immediately extracted with dichloromethane. The organic layer is washed with cold aqueous sodium hydrogencarbonate and cold water, dried, and evaporated in vacuo to give the title compound as a syrup (4.0 g., 91%); n.m.r. (chloroform-d): ∂ 6.63 (d, $J_{1,2}$ 4.0 Hz, H-1), 7.58–7.90 (4 aromatic), 1.96, 2.07 and 2.13 (3 OAc).

EXAMPLE IX 2,3,4-Tri-O-acetyl-6-deoxy-6-phthalimido-1-thio-β-D-galactopyranose (A) A solution of 2,3,4-tri-O-acetyl-6-deoxy-6-phthalimido-α-D-galactopyranosyl bromide (4.0 g.) and thiourea (0.67 g.) in dry acetone (20 ml.) is heated under reflux for 4 hours. The solution is evaporated in vacuo to a syrup which is partitioned between water and dichloromethane. The organic layer is re-extracted with water three times. The combined aqueous extracts are evaporated to 2-S-(2,3,4-tri-O-acetyl-6-deoxy-6-phthalimido-β-D-galactopyranosyl)-2-thiopseudourea (3.40 g.).

(B) Chloroform (9.0 ml.) is added to a solution of 2-S-(2,3,4-tri-O-acetyl-6-deoxy-6-phthalimido-β-D-galactopyranosyl)-2-thiopseudourea (3.4 g.) in water (10 ml.) containing potassium metabisulfite (1.38 g.). The mixture is heated with stirring under reflux for 15 minutes. The cooled solution is separated, and the organic layer is dried and evaporated in vacuo to give the title compound (2.5 g.). This material is used directly for the preparation of 6-(5-cholesten-3β-yloxy)hexyl 2,3,4-tri-O-acetyl-6-deoxy-6-ththalimido-1-thio-β-D-galactopyranoside.

EXAMPLE X 6-(5-Cholesten-3β-yloxy)hexyl 2,3,4-tri-O-acetyl-6-deoxy-6-phthalimido-1-thio-β-D-galactopyranoside Triethylamine (0.8 ml.) is added to a solution of 2,3,4-tri-O-acetyl-deoxy-6-phthalimido-1-thio-β-D-galactopyranose (2.5 g.) and 6-(5-cholesten-3β-yloxy)-hexyl iodide (3.3 g.) in dichloromethane (20 ml.). The solution is kept at room temperature under nitrogen overnight, and washed with water, dried, and evaporated in vacuo to a syrup (4.71 g.). This material is put on a column of silica gel and eluted with chloroform followed by 2% ethyl acetate in chloroform. The desired fractions are combined and evaporated in vacuo to give the title compound (4.0 g., 78%); $R_f$ 0.2 (CHCl$_3$—EtOAc. 95:5), $[\alpha]_d^{27}$ −93° C. (C 1.18, chloroform); n.m.r. (chloroform-d): ∂ 7.60–7.91 (4 aromatic), 1.93, 2.03, and 2.24 (3 OAc) 0.68 (CH$_3$—18).

EXAMPLE XI 6-(5-Cholesten-3β-yloxy)hexyl 6-amino-6-deoxy-1-thio-β-D-galactopyranoside A suspension of 6-(5-cholesten-3β-yloxy)hexyl 2,3,4-tri-O-acetyl-6-deoxy-6-phthalimido-1-thio-β-D-galactopyranoside (710 mg.) in methanol (10 ml.) and n-butylamine (10 ml.) is heated under reflux for 16 hours. The solution is evaporated to a crystalline mass. Chloroform is added and the solid is filtered and washed with chloroform. The combined filtrates are evaporated to a syrup which is put on a column of silica gel and eluted with chloroform-methanol-ammonium hydroxide (80:20:2). The desired fractions are combined and evaporated to a syrup which is triturated with ethyl ether to give crystals (390 mg. 76%); $R_f$ 0.28 (CHCl$_3$—MeOH—NH$_4$OH, 80:20:2), $[\alpha]_D^{27}$ −29.5° C. (C 1.05, chloroform), m.s.: m/e 665 (M$^+$ +1).

EXAMPLE XII 6-(5-Cholesten-3β-yloxy)hexyl 1-thio-β-L-fucopyranoside

A. 6-(5-Cholesten-3β-yloxy)hexyl 2,3,4-tri-O-acetyl-1-thio-β-L-fucopyranoside 2,3,4-Tri-O-acetyl-1-thio-β-L-fucopyranose (10 mmol) is treated with 6-(5-cholesten-3β-yloxy)hexyl iodide (10 mmol) in dichloromethane (30 ml) containing triethylamine (10 mmol). The reaction takes place in 1 day at room temperature under nitrogen. The resulting solution is washed with distilled water (20 ml) and dried with anhydrous sodium sulfate. The filtered solution is concentrated to form a syrup which is put on a silica gel column and eluted with chloroform followed by 1.0% ethanol in chloroform. The fractions containing the title compound, as determined by thin layer chromatography, are pooled and evaporated to give the title compound in 61% yield $[\alpha]_D$ −4° (c 1.5, chloroform).

B. 6-(5-Cholesten-3β-yloxyl)hexyl 1-thio-β-L-fucopyranoside

The blocked product from Step A is stirred with a basic ion exchange resin, Bio-Rad AG 1-X2(OH), in ethanol-tetrahydrofuran or sodium methoxide in methanol to give the title compound as needles, yield 80%, m.p. 110°–112° (ethyl acetate), $[\alpha]_D$ −11° (c 1.43, chloroform).

EXAMPLE XIII

Process for deblocking of neutral glycolipids

A solution of 1 equivalent glycolipid in 1:1 ethanol-THR (33 ml per g substrate) was treated with 2.5–3 fold excess Bio-Rad AG 1-X2 OH$^-$ion-exchange resin suspended in ethanol (16 ml per g substrate) and stirred 45 minutes at room temperature. The resin was filtered off and washed with warm THF (3×16 ml per g substrate), and the combined filtrates evaporated to give the following compounds:

6-(Cholest-5-en-3β-yloxy)hexyl 1-thio-α-D-manopyranoside (VIIb)

91% colorless needles (from THF), d.s.c. endothermic transitions: 64–65, 81–82, and 226°–227° C.; $[\alpha]_D^{25}$ +77.9°±0.9° (c 1.11 THF); IR 3600–3100 (OH) cm$^{-1}$; (s), 1105 (s), 1070 (s) cm$^{-1}$; MS: 665 (M+), 501, 368.

Anal. Cal. for C$_{39}$H$_{68}$O$_6$S: C, 70.44; H, 10.31; S, 4.82. Found: C, 70.20; H, 10.22; S, 4.80.

6-(Cholest-5-en-3β-yloxy)hexyl 1-thio-β-D-galactopyranoside (VIIa)

66% pale tan powder, m.p. 104°–106° C. (to liquid crystal) and 219°–221° C. (to isotropic liquid); IR 3600–3100 (OH) cm$^{-1}$.

Anal. Cal. for C$_{39}$H$_{68}$O$_6$S: C, 70,44; H, 10.31; S, 4.82. Found: C, 70.16; H, 10.03; S, 4.79.

EXAMPLE XIV 6-(5-Cholesten-3β-yloxy)hexyl 2-acetamido-2-deoxy-1-thio-β-D-galactopyranoside A. 6-(5-Cholesten-3β-yloxy)hexyl 2-acetamido-3,4,6-tri-O-acetyl-2-deoxy-1-thio-β-D-galactopyranoside The procedure of Example XII A is repeated except using 2-acetamido-3,4,6-tri-O-acetyl-2-deoxy-1-thio-β-D-galactopyranose (10 mmol) in lieu of 2,3,4-tri-O-acetyl-1-thio-β-L-fucopyranose, and using 1,5-diazabicyclo[5.4.0]-undec-5-ene (10 mmol) in place of triethylamine. The compound is obtained as a crystalline material, yield 43%, m.p. 130°-133° (ethanol), $[\alpha]_D$ −37° (c 1.5, chloroform).

B. 6-(5-Cholesten-3β-yloxy)hexyl 2-acetamido-2-deoxy-1-thio-β-D-galactopyranoside The title compound is obtained following the procedure of Example XII B, yield 85%, m.p. 241°-243°, $[\alpha]_D$ −35° (c 1.5, N,N-dimethylformamide).

EXAMPLE XV

Preparation of 2,3,4-tri-O-acetyl-6-O-methylsulfonyl-α-D-mannopyranosyl Bromide

An ice-cold solution of 14.9 g (34.9 mmol) 1,2,3,4-tetra-O-acetyl-6-O-methylsulfonyl-6β-D-mannopyranose prepared by the process set forth in J. Fernandez-Bolanos and R. G. Fernandez-Bolanos, *An. Quim.*, 65 (1969) 1163–1164; *Chem. Abstr.*, 72 (1970) 133105w in 60 ml dry $CH_2Cl_2$ was treated with 21 ml 30–32% HBr in glacial AcOH, and kept 2.5 hours at 25° C. The mixture was poured into 400 ml stirred ice water, separated, and the aqueous phase washed with three 20 ml aliquots of $CH_2Cl_2$. The combined organic layers were washed with water and saturated $NaHCO_3$, dried with $Na_2SO_4$, evaporated, triturated with petroleum ether (bp 30°–60° C.), filtered, and air dried to leave 14.6 g (93%) of the solid α-glycosyl bromide IX, m.p. 167.5–168.5° C. (dec); $[\alpha]_D^{25}$ +120.0°±0.05° (c 1.01 $CHCl_3$); IR 1740 and 1725 (acetate) cm$^{-1}$.

Anal. Calc. for $C_{13}H_{19}BrO_{10}S$: C, 34.91; H 4.28; Br, 17.87; S, 7.17. Found: C, 35.04; H, 4.18; Br, 17.61; S, 7.27.

EXAMPLE XVI 6-(Cholest-5-en-3β-yloxy)hexyl 2,3,4-tri-O-acetyl-6-azido-6-deoxy-1-thio-α-D-mannopyranoside (XIII)

The mannosyl bromide prepared by the process set forth in Example XV was converted via the isothiouronium bromide X [85%, white powder, m.p. 87°-90° C. (dec); IR 3600–3100, 1740, 1640 cm$^{-1}$] to the corresponding thiol XI [89% colorless glass, IR 2560, 1750–1730 cm$^{-1}$] according to the process set forth in M. Cerny, J. Stanek and J. Pacak, *Monatsh.* 94 290–294 (1963). The thiol XI was coupled with IV as in Example IX to provide 61% 6-(cholest-5-en-3β-yloxy)-hexyl 2,3,4-tri-O-acetyl-6-D-methylsulfonyl-1-thio-α-D-mannopyranoside (XII), a white glass, IR 1740 cm$^{-1}$. Finally, 1.14 g (1.32 mmol) of the preceding mesylate, 0.49 g (7.5 mmol) $NaN_3$, and 40 ml dry DMF were stirred together at 70°–75° C. under $N_2$ for 4.5 hours. After evaporating the solvent, the residue was dissolved in 20 ml ether, washed with three 10 ml portions of $H_2O$, dried with $MgSO_4$, and evaporated to leave 1.05 g (97%) title azide XIII as a colorless glass, homogenous on TLC (12% EtOAc in benzene on silica gel), $[\alpha]_D^{25}$ +12.6°±0.5° (c 1.02 $CHCl_3$); IR 2095 (azide), and 1755 (acetate) cm$^{-1}$. A 0.54 g sample was further purified by column chromatography (silica gel, 12% EtOAc in benzene), providing 0.417 g (75% yield), colorless glass which solidified on prolonged standing, m.p. 68°-70° C.

Anal. Calc. for $C_{45}H_{73}N_3O_8S$: C, 66.22; H, 9.02; N, 5.15; S, 3.93. Found: C, 66.53; H, 8.98; N, 5.04; S, 3.98.

EXAMPLE XVII

Preparation of 6-(Cholest-5-en-3β-yloxy)hexyl 6-azido-6-deoxy-1-thio-α-D-mannopyranoside (XIV)

Azido triacetate XIII was deblocked by the process set forth in Example X to provide 62% of the title azido triol XIV as a glass, IR 3600–3100 (OH), 2095 (azide) cm$^{-1}$.

Anal. Calc. for $C_{39}H_{67}N_3O_5S$: C, 67.88; H, 9.79; S, 4.65. Found C, 67.80; H, 9.55; S, 4.54.

EXAMPLE XVIII

Preparation of 6-Cholest-5-en-3β-yloxy)hexyl 6-amino-6-deoxy-1-thio-α-D-mannopyranoside (VIId)

A solution of 0.163 g (0.236 mmol) of the azido triol prepared by the process set forth in Example XVII in 4.0 ml $CHCl_3$ containing 3.0 ml triethylamine was treated with dry gaseous $H_2S$ at room temperature for 4.5 hours. The volatile components were removed by rotary evaporation and the product isolated by preparative TLC (silica gel, 7:2:1 $CHCl_3/CH_3OH$/conc. aqueous $NH_3$) to yield 65.0 mg (41%) white powder, m.p. indef.; IR 3650 ($NH_2$), 3600–3100 (OH) cm$^{-1}$; MS: 635 (M$^+$—$CH_2$=NH$^+$), 503, 470, 386, 368, 353. A 1 mg sample was per-O-trimethylsilylated with bis(trimethylsilyl)trifluoroacetamide in DMF at 65°-70° C. for 15 minutes, MS: 1024 (M$^+$), 1009, 951 (M$^+$-TMS), 936, 921, 850 M$^+$—N(Si[$CH_3$]$_3$)$_2$, 523, 501, 368, 174 (base peak). A high resolution MS of the per-O-trimethylsilylated saccharide fragment was taken.

Anal. Calc. for $C_{21}H_{52}NO_4Si_5^+$: 522.2744. Found 522.2721.

Having fully described the invention, it is intended that it be limited only by the lawful scope of the appended claims.

We claim:

1. Phospholipid vesicles comprising a lipid bilayer which includes:
   a cell-surface receptor selected from synthetic sugar and amino sugar derivatives of cholesterol, and cholesterol, and
   an effective amount of physiologically compatible radioactive tracer, cytotoxic or therapeutic agent as a part of the vesicles.

2. Phospholipid vesicles of claim 1 wherein the cell-surface receptor is selected from the group consisting of, 6-(5-cholesten-3β-yloxy)hexyl 1-thio-β-L-fucopyranoside, 6-(5-cholesten-3β-yloxy)hexyl 1-thio-β-D-galactopyranoside, 6-(5-cholesten-3β-yloxy)hexyl 1-thio-α-D-mannopyranoside, 6-(5-cholesten-3-yloxy)-hexyl 2-acetamido-2-deoxy-1-thio-β-D-galactopyranoside, 6-(5-cholesten-3β-yloxy)hexyl 6-amino-6-deoxy-1-thio-β-D-galactopyranoside and 6-(5-cholesten-3β-yloxy)hexyl 6-amino=6-deoxy-1-thio-α-D-mannopyranoside.

3. Phospholipid vesicles of claim 1 wherein the cell-surface acceptor is:
   6-(5-cholesten-3β-yloxy)hexyl 6-amino-6-deoxyl-1-thio-β-D-galactopyranoside.

4. Phospholipid vesicles of claim 1 wherein the cell-surface acceptor is:
   6-(5-cholesten-3β-yloxy)hexyl 6-amino-6-deoxy-1-thio-α-D-mannopyranoside.

5. The method comprising administering to the mammalian host phospholipid vesicles comprising a lipid-bilayer which includes:
- a cell surface receptor selected from synthetic sugar and amino sugar derivatives of cholesterol, and cholesterol, and
- an effective amount of physiologically compatible radioactive tracer, cytotoxic or therapeutic agent as a part of the vesicles,
- said phospholipid vesicles being further characterized by the rapid intact accumulation in the lymphatic system and/or lungs, spleen or liver.

6. The method of claim 5 wherein the cell-surface receptor is selected from the group consisting of 6-(5-cholesten-3β-yloxy)hexyl 1-thio-β-L-fucopyranoside, 6-(5-cholesten-3β-yloxy)hexyl 1-thio-β-D-galactopyranoside, 6-(5cholesten-3β-yloxy)hexyl 1-thio-α-D-mannopyranoside, 6-(5-cholesten-3β-yloxy)hexyl 2-acetamido-2-deoxy-1-thio-β-D-galactopyranoside, 6-(5-cholesten-3β-yloxy)hexyl 6amino-6-deoxy-1-thio-β-D-galactopyranoside and 6-(5-cholesten-3β-yloxy)hexyl 6-amino-6-deoxy-1-thio-α-D-mannopyranoside.

7. The method of claim 5 where the cell-surface acceptor is:
6-(5-cholesten-3β-yloxy)hexyl 6-amino-6-deoxy-1-thio-β-D-galactopyranoside.

8. The method of claim 5 wherein the cell-surface acceptor is:
6-(5-cholesten-3β-yloxy)hexyl 6-amino-6-deoxy-1-thio-α-D-mannopyranoside.

* * * * *